United States Patent [19]
Streichenberger

[11] Patent Number: 6,056,476
[45] Date of Patent: May 2, 2000

[54] NEAR OFF-BOTTOM CULTIVATION OF KELP FORESTS

[76] Inventor: Rodolphe Streichenberger, 75 Sea Island Dr., Newport Beach, Calif. 92660

[21] Appl. No.: 09/206,276

[22] Filed: Dec. 7, 1998

Related U.S. Application Data

[63] Continuation-in-part of application No. 09/102,820, Jun. 23, 1998, abandoned.

[51] Int. Cl.[7] .............................. E02B 3/04; A01G 7/00; A01H 13/00
[52] U.S. Cl. .................. 405/24; 47/59; 405/23; 405/25; 119/208; 119/221
[58] Field of Search .................. 405/24, 22, 23, 405/25; 119/208, 221; 47/58, 69, 57.6, 56, 47, 59

[56] References Cited

U.S. PATENT DOCUMENTS

| | | | |
|---|---|---|---|
| 3,648,464 | 3/1972 | Edwards | 405/24 |
| 4,130,994 | 12/1978 | Van Moss | 405/24 |
| 4,854,774 | 8/1989 | Streichenberger | 405/24 X |
| 4,872,782 | 10/1989 | Streichenberger | 405/24 |
| 5,201,141 | 4/1993 | Ahm | 47/67 |
| 5,451,443 | 9/1995 | Wechsler | 47/69 X |

*Primary Examiner*—Dennis L. Taylor

[57] ABSTRACT

A combination of old and new features to cultivate seaweed on the sea bottom comprising the steps of cultivating in a laboratory sporophytes and fixing them on lines, setting anchors on various water bottoms, installing near off-bottom artificial substrates, and transferring the pre-cultivated sporophytes onto these substrates. The complete method allows young seaweed and young kelp to survive the exaction of bottom and off-bottom grazing predators and interspecies competition.

2 Claims, 2 Drawing Sheets

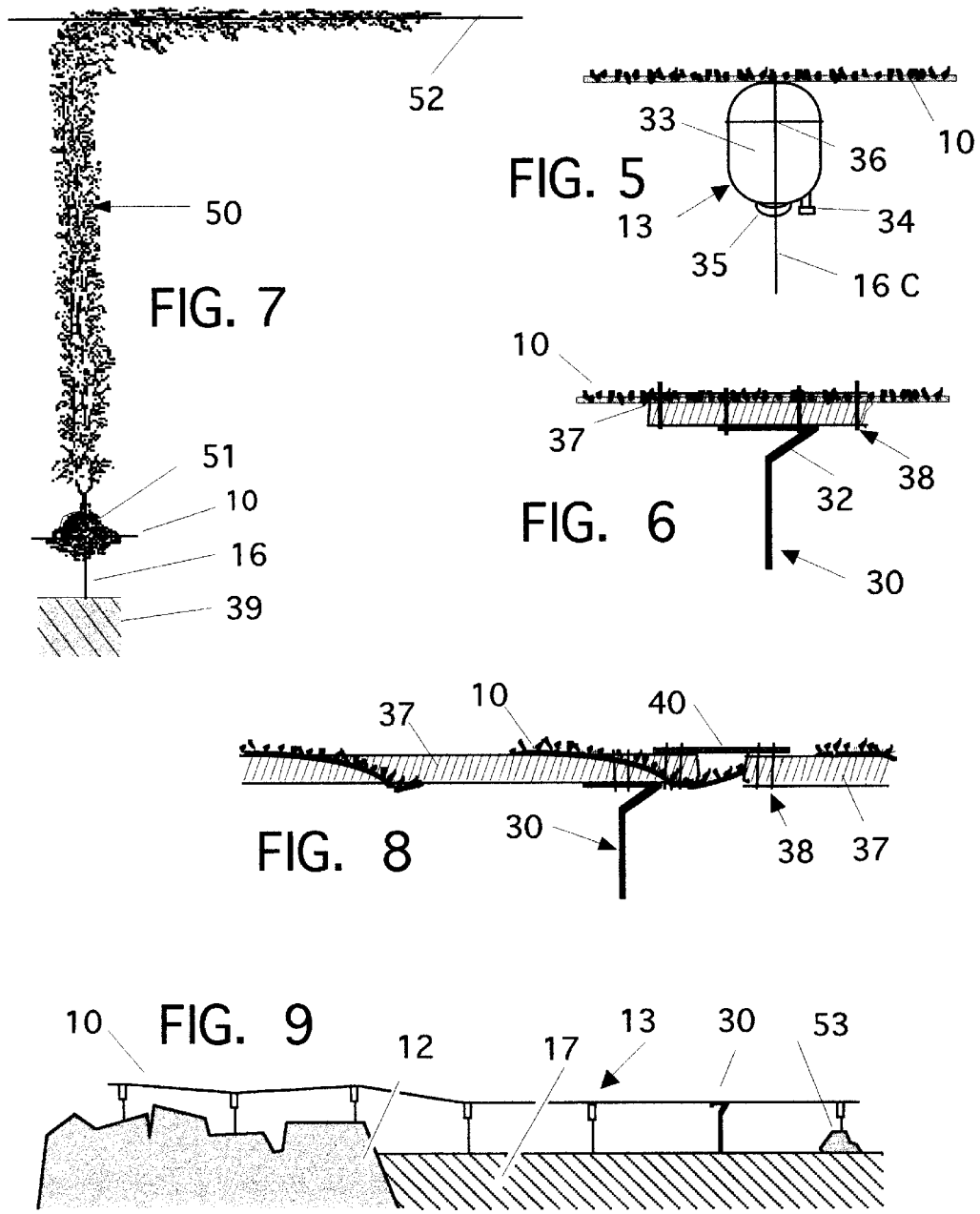

NEAR OFF-BOTTOM CULTIVATION OF KELP FORESTS

This application is a continuation-in-part of application Ser. No. 09/102,820, filed Jun. 23, 1998, now abandoned.

BACKGROUND OF INVENTION

This invention relates to the aquaculture of seaweed, specifically to the method of planting and cultivating large acreage of kelp forests on various water bottoms.

BACKGROUND—DESCRIPTION OF PRIOR ART

Seaweed have long been cultivated for food consumption and for the production of alimentary and pharmaceutical products. Otherwise, important developments are now expected with the cultivation of kelp species for the replacement of lost marine habitats and the production of marine biomass for energy. In California, the human-caused loss of about half of the kelp forests since 1950 is calling for renewed efforts in the art of restoring and expanding on a large scale depleted kelp forests.

For human consumption, seaweed are commonly cultivated on pre-cultivated lines immersed under the surface of the sea. For example, the culture of *Undaria pinnatifida* begins in a land-based laboratory wherein sporophytes are born and affixed on thin lines. Later, sporophyte lines are deployed in open sea and coiled around thicker lines which are suspended horizontally under buoys. These culture lines are easily lifted to the water surface for survey, maintenance, and yield of the crop.

This system in suspension works with seaweed of small, neutral, or negative buoyancy such as *Undaria pinnafitida* which does not ascend by itself in the water column but as a matter of fact hangs head down under the culture lines. However, this system in suspension does not work with seaweed which are buoyant by the effect of their pneumatocysts, the gaz-filled membranes which make them float. For example, in the culture of the giant kelp *Macrocystis pyrifera* which has pneumatocysts, a line of laboratory-cultivated sporophytes cannot be placed in suspension under buoys because it would rise to the surface at the first development of the plants' pneumatocysts, and once floating on the surface *Macrocystis pyrifera* would die.

In 1984, my son Antonius Streichenberger has proposed a method for cultivating Macrocystis species on pre-seeded thick lines of which the flotation level would have been only controlled by the buoyant effect of the pneumatocysts of the plants as described and published in Apr. 24, 1985 under the international reference WO 86/02395. The proposition was abandonned when it was realized that the system with thick lines or ropes not supported by buoys or floats was at risk to sink to the bottom after colonization by mussels.

In 1987, Antonius Streichenberger proposed a water jet method for implantation of aquacultural artificial substrates on sedimentary bottoms. On Aug. 8, 1989, the invention was granted the U.S. Pat. No. 4,854,774. This invention is effective to keep seaweed and mussels out of reach of bottom grazers such as urchins and starfish. Unfortunately the invention does not protect seaweed from the destructive grazing activity of fish such as opaleyes and halfmoons. Another drawback is that the water jet anchoring system does not allow the anchoring of substrates on rocky bottoms which is a serious inconvenience since rocky bottoms are natural places of the growth of kelp.

In 1989, I was granted the U.S. Pat. No. 4,872,782 which can be used for the implantation of aquacultural artificial substrates which are buoyant. Unfortunately, this invention, which works for the culture of mussels, does not work for the cultivation of seaweed because of the already-mentionned problem of fish grazing. Also the waterjet mooring system does not work on rocky bottoms as already mentionned above.

In 1994, I was granted the U.S. Pat. No. 5,370,476 wherein a self anchoring tire-made artificial reef serves as a bottom habitat and also can serve to anchor a floating artifical substrate for the fixation of kelp. Unfortunately, this embodiment of the invention does not protect kelp from already-mentionned exaction by grazing fish.

In Apr. 17, 1998 the applicant filed another patent application Ser. No. 09/063,298 proposing to plant laboratory-cultivated kelp seedlings directly on rock by clipping the seedlings on small protuberances which are numerous on rock such as the small stem of a dead or alive sea fan, the calciferous skeleton of a sessile organism, or the sharp asperity of the rock. Unfortunately this system, which solves the problem of fixing kelp plants on rock, does not solve the problem of off-bottom grazing fish, and worse it encounters the problem of bottom-grazing by invertebrates such as urchins. Urchins can fastly devore entirely the blades of young seaweed as well as the holdfasts of adult giant kelp.

In 1996 the California Department of Fish and Game, reviewing kelp restoration methods on rocky and sandy bottoms since 1963, wrote a history of techniques experimented in California for the purpose (1) of controlling grazers, (2) transplanting kelp, (3) securing plants in soft sediment habitats, and (4) controlling competitive seaweed. None of these techniques solved the whole of the above-mentionned problems, and most of these techniques were unsatisfactory.

The Prior Art has not solved the main problems of kelp restoration from anchoring artificial substrates on various sandy or rocky bottoms, to bottom grazing by creeping predators and off-bottom grazing by swimming predators, and to colonization of artificial substrates by mussels.

OBJECTS AND ADVANTAGES OF THE INVENTION

Accordingly, several objects and advantages of my invention are:

(a) to cultivate seaweed on off-bottom artificial substrates out of reach of bottom grazers;

(b) to cultivate seaweed on near-bottom artificial substrates not colonized by mussels;

(c) to cultivate seaweed on sandy bottoms and on rocky bottoms;

(d) to cultivate seaweed on rocky bottoms where relieves and cavities make a habitat for large invertebrates such as lobsters and octopus wherein these invertebrates benefit greatly in feeding on living organisms fallen from the marine life above.

(e) to install underwater massive quantities of pre-cultivated sporophytes in order to obtain a sufficient number of plants surviving the exaction of grazing fish.

(f) to obtain all the above-mentioned avantages in one method adaptable to various conditions of water bottom and water conditions.

Further objects and advantages are in the possibility to restore kelp beds at the very same rocky places where once before they flourished. Advantageous also is the fact that the invention can be used for both the aquaculture of small and large seaweed. Another advantage exists in the simplicity of using small boats and light materials for planting operations. Further objects and advantages will become apparent from a consideration of the ensuing description and drawings.

DRAWING FIGURES

FIG. 5 shows how a floating substrate is connected to a sporophyte line.

FIG. 6 shows how a standing substrate is connected to a sporophyte line.

FIG. 7 shows a giant kelp grown on a substrate above bottom.

FIG. 8 shows a thick rope and a sporophyte line deployed in-between substrates

FIG. 9 shows floating and standing substrates on rocky and sandy bottoms.

Figure 1:
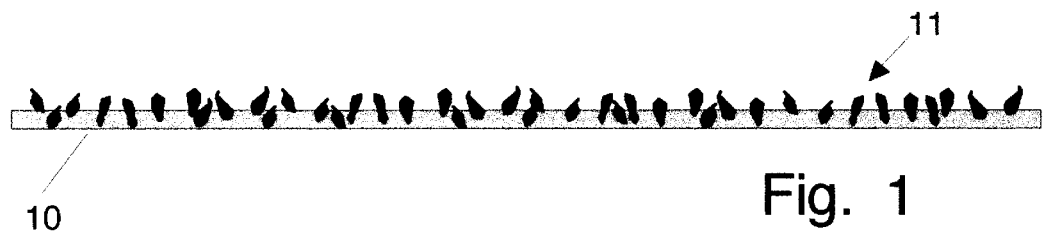
FIG. 1 shows a sporophyte line.

REFERENCE NUMERALS IN DRAWINGS 10 sporophyte line
11 sporophytes
12 rock
13 floating substrate or float
14 hole
15 eyebolt or anchor
16 mooring line
17 sand
18 burried anchor
30 standing substrate
31 angle shape
32 T shape
33 container
34 tap opening
35 handle
36 fasteners
37 support surface rope
38 attachments
39 bottom of rock or sand
40 connecting line
50 kelp plant
51 kelp holfast
52 sea surface
53 heavy rock or mooring

SUMMARY

A combination of old and new features to plant kelp on rocky and sandy bottoms comprising the steps of cultivating in a laboratory sporophytes and fixing them on lines, setting anchors, installing artificial substrates, and transferring the pre-cultivated sporophytes on the substrates.

DETAILED DESCRIPTION OF THE INVENTION

FIG. 1 shows a thin line (10) on which laboratory-cultivated sporophytes (11) have been affixed in the laboratory. This sporophyte line (10) of about 2 or 3 mm. in diameter is spooled on a frame or bobbin before to be deployed at sea.

Figure 2:
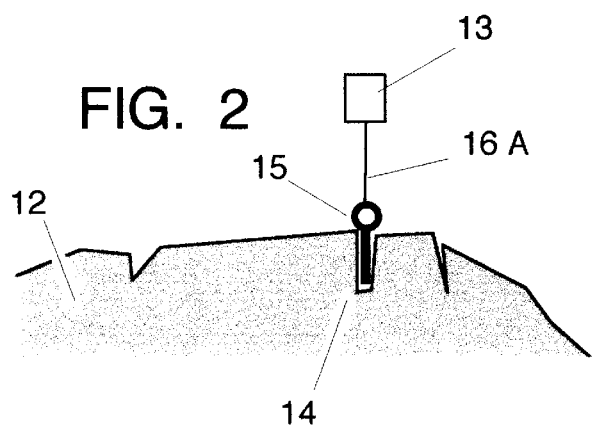
FIG. 2 shows how a floating substrate is anchored on rock.

FIG. 2 shows a rock (12) in which a hole (14) has been drilled and wherein an eyebolt or anchor (15) has been set. Floating substrate or float (13) is moored on anchor (15) on rock (12) by a mooring line (16 A).

Figure 3:
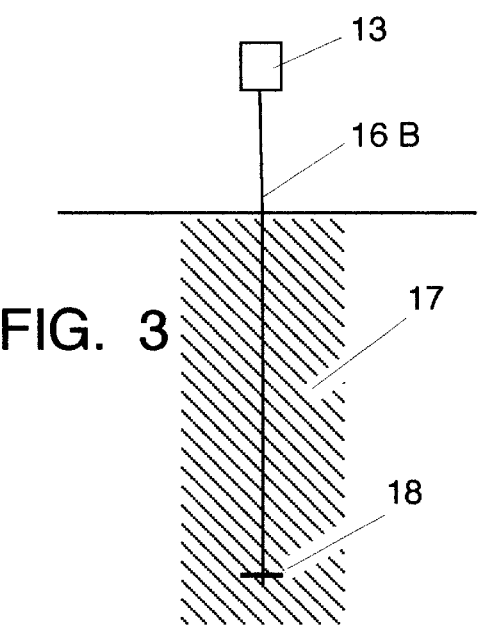
FIG. 3 shows how a floating substrate is anchored on sand.

FIG. 3 shows a floating substrate (13) moored into a sandy bottom (17) by a partially burried mooring line (16 B) and a burried anti-extractive device or anchor (18) which is a small plate of plastic or iron.

Figure 4:
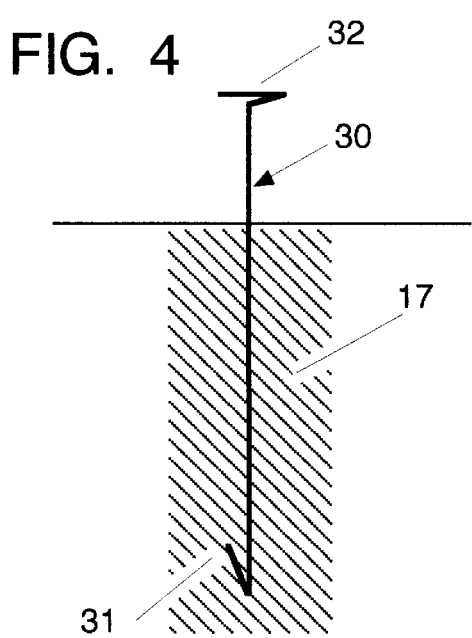
FIG. 4 shows how a standing substrate is anchored on sand.

FIG. 4 shows a partially burried bar (30) standing above a sandy bottom (17). Bar (30) has an anti-extractive shape (31) at its lower end and a support-surface T shape (32) at its upper end.

FIG. 5 shows floating substrate (13) made by a container (33) with a tap opening (34) and an handle (35) where is fixed mooring line (16 C). Above floating substrate (13) is seen a part of sporophyte line (10) attached to container (33) by fasteners (36).

FIG. 6 shows the upper part of standing substrate (30) on which a T shape support-surface (32) for the fixation of kelp on which a piece of rope (37) is attached by fasteners (38). Above rope (37) is seen attached a part of sporophyte line (10).

FIG. 7 shows a giant kelp plant *Macrocystis pyrifera* (50) of which the holdfast (51) has grown over unseen floating substrate (13) or standing substrate (30) moored on a rocky or sandy bottom (39). The upper part of Kelp (50) floats at the surface of the sea (52).

FIG. 8 shows a thick rope (37) and a sporophyte line (10) coiled around thick rope (37). Thick rope (37) is deployed from one substrate (30) to another substrate not shown in figure (8). At the end of rope (37) a thin line (40) is fastened to rope (37) by attachments (38) and connected to another rope (37).

FIG. 9 shows a sporophyte line (10) which has been deployed and attached on three floating substrates (13) anchored on rock (12), two floating substrates (13) moored in sand (17), one standing substrate (30) moored in sand (17), and one floating substrate (13) moored on a heavy rock (53).

A first operation of the invention is the production of sporophytes in a land-based laboratory and the fixation of these sporophytes on sporophyte lines (10), preferably buoyant. The technique is known mainly from the works of J. W. Chang (1970), J. W. Kang (1977), G. S. Hue (1981), R. Perez (1994), and other algologists.

A second operation consists of setting anchors on a water bottom which is expected to change from rock to sand, or any other kind of hard or soft substrate, particularly when the plantation program extends on large acreage.

When meeting with rock (12), a diver equipped with a drilling tool as for example an hydraulic rotary hammer which works underwater, follows a preset guideline, drills from place to place holes (14) in the rock, and screws eyebolts or anchors (15) in holes (14). The pneumatic hammer is activated by an air compressor installed on a boat at the water surface.

When meeting with sand (17), a diver equipped with an excavating pipe conveying pressurized water or waterjet, follows a preset guideline, diggs from place to place the sedimentary bottom by forcing water through said water jet, and sets in mooring lines (16) with an anti-extraction device (18) about 3 feet deep, as it has been described in my U.S. Pat. No. 4,872,782.

In a third operation the diver sinks containerlike floating substrates (13) temporarily filled with water and moor them with mooring lines (16) which have been anchored in rock (12) or in sand (17), and then the diver refills said substrates with air to make them float. A good floating substrate (13) for the giant kelp *Macrocystis pyrifera* can be a fuel container of 6 gallon capacity. Floating substrates can also be made of low density material suck as synthetic foam which floats by itself in the water. Also, for example, a floating substrate can be made of a thick polypropylene rope which is buoyant.

In a preferred embodiment, when meeting with a sedimentary bottom as sand or mud, the diver waterjets into the soft bottom thin and lengthy elements or standing substrates (30) with anti-extraction shapes or devices (31) whereby said lengthy elements protrude and stand above and close to the bottom. A standing substrate (30) can be a solid bar with an angle shape (31) at its lower end and a T shape (32) at its upper end.

The mooring elements of above-mentionned floating or standing substrates have the same following characteristic: they are thin. On these flexible or rigid thin elements creeping invertebrates do not climb easily and mussels do not colonize easily.

In a fourth operation the diver deploys sporophyte lines (10), preferably buoyant, and tie them to the top of each floating substrate (13) or standing substrate (30).

On lines (10) are affixed a great number of kelp sporophytes (11), for example 300 per meter, which are not visible in FIG. 1. Out of said 300 laboratory-cultivated sporophytes about 20 small kelp plants per meter will develop safe from bottom creeping grazers as urchins but anyhow grazed upon by above-bottom swimming grazers as fish opaleye and halfmoon. After some time, in each interval between substrates (13) or (30), enough small plants will survive to make at least one plant growing on each substrate (13) or (30) or at least available to be transferred on a substrate (13) or (30). It is expected that sporophytes (11) next to the point of attachment of line (10) on substrate (13) or (30) will affix and develop faster on the substrate's larger surface than sporophytes affixed on thin line (10)). Fast growing plants, hopefully affixed on substrate (13) or (30), will shade slow-growing plants, stop their growth, and leave them be grazed out by grazing fish. For example, in the culture of the giant kelp *Macrocystis pyrifera* a sporophyte line (10) deployed on substrates (10) or (30) every 3 meters, with about 1,000 affixed sporophytes (11) every 3 meters, should result in the final production of at least one adult plant which will have overpassed all other plants, shading them, stopping their growth, and finally determining their fate as decoys to be eaten by grazers. In average natural conditions the density of fully grown Macrocystis plants in a kelp forest should be of about 900 plants per hectare.

A risk of colonization of sporophyte lines (10) by mussels is prevented by the thinness of lines (10), about 2–3 mm. diameter lines. Colonization by mussels of strongly floating substrates (10) or strongly standing substrates (30) does not alter the stability of said substrates which support lines (10).

Lines (10) and their laboratory-affixed sporophytes (11) can be easily and cheaply replaced by divers as many times as needed, as the plantation success or failure depends on availability of water nutrients, grazing pressure, and storm impact.

A particular embodiment of the invention consists of cultivating and affixing on the same sporphyte line (10) in the laboratory two or more different strains of seaweed. This diversity of strains increases the probability of success in a planting operation. For example, in the ignorance of climatic conditions ahead, the aquaculturist has advantage to have on the same sporophyte line (10) a strain of California Macrocystis for cold water and a strain of Mexico Macrocystis for warm water.

Another embodiment of the invention consist of cutting out one or several segments of a line (10) with each segment having a plant affixed upon and transferring segments and plants onto substrates (13) or (30)) which have not plants affixed upon.

Another embodiment consists of deploying in-between and on artificial substrates (13) or (30) a thick rope (37), for example, a 5 cm. diameter, polypropylene rope which floats in the water, and to coil around this rope (37) a laboratory-cultivated thin sporophyte line (10). This will allow the cultivation of plants on substrate lines more strong than the fragile 2–3 mm. diameter sporophyte lines (10) from the laboratory. In that case, a greater risk of mussel colonization exists and must be compensated by stronger floating and standing substrates (10) and (30).

Another particular embodiment of the invention consists of deploying and attaching only segments of above-mentionned large diameter rope (37) above and between two artificial substrates (13) or (30). The attachment of these segments of rope between themselves and on substrates (13) or (30) is made with smaller diameter attachment lines (40) or (38) in order to allow these attachments (40) or (38) to break and free the segments of rope (37) from substrates (13) or (30) if these segments happen to be caught and pulled out by the anchor of a boat.

Another embodiment of the invention consists of dropping on the water floor heavy moorings (53) which will stand on the bottom. On this other kind of anchor, mooring lines (16) of floating substrates (13) can be attached. Also, a large diameter buoyant rope (37) can be moored by a mooring line (16) on heavy moorings (53) and deployed above and between these moorings, and a sporophyte line (10) can be coiled around large diameter rope (37). These heavy moorings (53) can be, for example, heavy rocks, concrete blocks, prefabricated devices, or various recycled materials. Heavy moorings (53) function as bottom habitat for fish, invertebrates, and sessile organisms; they can be of various shapes and they can be hollow.

CONCLUSION, RAMIFICATIONS, AND SCOPE OF THE INVENTION

Thus, the reader will see that my invention for the off-bottom plantation and cultivation of kelp forests is a combination of separate old and new features which are: pre-cultivated sporophytes affixed on lines, close-to-bottom floating or standing substrates, and anchors set in or on sand or rock. The invention combines these features in a novel way which lessens or eliminates long-deplored problems in seaweed cultivation. The invention allows a renewable endless source of young plants to be planted and cultivated in nutrient-rich coastal waters while surviving the exaction of bottom and off-bottom grazers, and growing on substrates not easily colonized by mussels.

In spite of thirty years of research for the restoration of kelp forests such a successful combination of old and new features was never found by prior-art workers.

The invention allows the off-bottom plantation of seaweed fields or kelp forests on large acreage of various water bottoms made of sand, mud, rock, coble, and mixed materials. The invention is useful for the aquaculture of seaweed for human consumption and for the industry of alimentary, pharmaceutical, and fertilizing products. The invention is also useful for the production of vegetal biomasses, for the creation of fish habitats, and for the production of renewable energy.

While my above description contains many specificities, these should not be construed as limitations on the scope of the invention but rather as an examplification of the preferred embodiments thereof. Many other variations are possible. For example, the installation of sporophyte lines (10) are wrapped around rather than deployed in between artificial substrates (13) or (30), or the artificial substrates (13) or (30) are equipped with clips which allow the quick fastening of sporophyte lines (10).

Accordingly, the scope of the invention should be determined not by the embodiments illustrated, but by the appended claims and their legal equivalents.

I claim:

1. A method for planting seaweed on rocky and sedimentary water bottoms comprising the steps of:

cultivating in a laboratory seaweed sporophytes and fixing them on lines;

setting anchors on the water floor;

mooring on the anchors and close to the bottom artificial substrates for the fixation of seaweed;

transferring the lines of sporophytes from the laboratory to the sea;

attaching the lines of sporophytes on the artificial substrates; and replacing the sporophyte lines as often as needed for the development of a satisfactory density of adult plants on the floating substrates and on the lines.

2. A method according to claim 1 wherein a larger diameter buoyant rope is deployed in-between and on artificial substrates which are near off-bottom and wherein laboratory-cultivated lines of sporophytes are coiled around this rope.

* * * * *